(12) United States Patent
Bylemans et al.

(10) Patent No.: US 9,538,754 B2
(45) Date of Patent: *Jan. 10, 2017

(54) COMBINATIONS OF PYRIMETHANIL AND MONOTERPENES

(71) Applicant: Janssen Pharmaceutica NV, Beerse (BE)

(72) Inventors: Dany Leopold Jozefien Bylemans, Hasselt (BE); Jan Pieter Hendrik Bosselaers, Beerse (BE)

(73) Assignee: Janssen Pharmaceutica NV, Beerse (BE)

( * ) Notice: Subject to any disclaimer, the term of this patent is extended or adjusted under 35 U.S.C. 154(b) by 0 days.

This patent is subject to a terminal disclaimer.

(21) Appl. No.: 15/071,493

(22) Filed: Mar. 16, 2016

(65) Prior Publication Data

US 2016/0192654 A1    Jul. 7, 2016

Related U.S. Application Data

(62) Division of application No. 14/753,322, filed on Jun. 29, 2015, now Pat. No. 9,320,275, which is a division of application No. 14/164,749, filed on Jan. 27, 2014, now Pat. No. 9,119,399, which is a division of application No. 13/703,045, filed as application No. PCT/EP2011/059572 on Jun. 9, 2011, now Pat. No. 8,691,834.

(30) Foreign Application Priority Data

Jun. 10, 2010  (EP) .................................. 10165463

(51) Int. Cl.
| | |
|---|---|
| A01N 43/54 | (2006.01) |
| A01N 35/06 | (2006.01) |
| A01N 31/08 | (2006.01) |
| A01N 31/06 | (2006.01) |
| B27K 3/34 | (2006.01) |
| B27K 3/38 | (2006.01) |
| B27K 3/50 | (2006.01) |

(52) U.S. Cl.
CPC ............. *A01N 43/54* (2013.01); *A01N 31/06* (2013.01); *A01N 31/08* (2013.01); *A01N 35/06* (2013.01); *B27K 3/343* (2013.01); *B27K 3/38* (2013.01); *B27K 3/50* (2013.01)

(58) Field of Classification Search
USPC ........................................................ 514/275
See application file for complete search history.

(56) References Cited

U.S. PATENT DOCUMENTS

| | | | |
|---|---|---|---|
| 4,061,750 A | 12/1977 | Lada et al. | |
| 4,945,087 A * | 7/1990 | Talwar | A61K 8/347 424/49 |
| 6,156,760 A | 12/2000 | Muller et al. | |
| 2004/0244639 A1 | 12/2004 | Narayanan | |
| 2006/0086283 A1 | 4/2006 | Ray | |
| 2007/0224289 A1 | 9/2007 | Clausen et al. | |

FOREIGN PATENT DOCUMENTS

| | | |
|---|---|---|
| EP | 0224339 B1 | 1/1991 |
| WO | WO 98/54279 A1 | 12/1998 |
| WO | WO 03/011030 A1 | 2/2003 |
| WO | WO 2005/058320 A1 | 6/2005 |
| WO | WO 2006/045751 A1 | 5/2006 |
| WO | WO 2006/047126 A2 | 5/2006 |
| WO | WO 2006/086283 A1 | 8/2006 |
| WO | WO 2009/030744 | 3/2009 |
| WO | WO 2009/098243 | 8/2009 |

OTHER PUBLICATIONS

International Search Report from related International Patent Application No. PCT/EP2011/059572: Mailing date of International Search Report: Apr. 26, 2012.
International Search Report from related International Patent Application No. PCT/EP2009/051290: Mailing date of International Search Report: Jun. 4, 2009.
Written Opinion of the International Searching Authority from related International Patent Application No. PCT/EP2009/051290: Mailing date of Written Opinion: Jun. 4, 2009.
International Search Report from related International Patent Application No. PCT/EP2008/061765: Mailing date of International Search Report: Nov. 11, 2008.
Written Opinion of the International Searching Authority from related International Patent Application No. PCT/EP2008/061765: Mailing date of Written Opinion: Nov. 11, 2008.
Kull et al., "Mixtures of quaternary ammonium compounds and long-chain fatty acids as antifungal agents.", Applied Microbiology, 1961, pp. 538-541, vol. 9.
Zwart Voorspuij, A.J., and C.A.G. Nass , "Some aspects of the notions additivity, synergism and antagonism in the simultaneous activity of two antibacterial agents in vitro.", Arch. intern. Pharmaco-dynamie, 1957, pp. 211-228, vol. 109.
Steinberg, D.C., "Measuring synergy.", Cosmetics & Toiletries, 2000, pp. 59-62, vol. 115(11).
Silvestry-Rodriguez et al., "Silver as a Disinfectant.", Rev. Environ. Contam. Toxicol, Jul. 27, 2007, p. 23-45, vol. 191.

* cited by examiner

*Primary Examiner* — Kathrien Cruz

(57) ABSTRACT

The present invention relates to combinations of pyrimethanil, or a salt thereof, and a monoterpene, or a salt thereof, which provide an improved biocidal effect. More particularly, the present invention relates to compositions comprising a combination of pyrimethanil, or a salt thereof, together with a monoterpene selected from thymol and β-thujaplicin in respective proportions to provide a synergistic biocidal effect. Compositions comprising these combinations are useful for the protection of any living or non-living material, such as crops, plants, fruits, seeds, objects made of wood, thatch or the like, engineering material, biodegradable material and textiles against deterioration due to the action of microorganisms such as bacteria, fungi, yeasts, algae, viruses, and the like.

3 Claims, No Drawings

COMBINATIONS OF PYRIMETHANIL AND MONOTERPENES

CROSS REFERENCE TO RELATED APPLICATIONS

This application is a divisional of U.S. application Ser. No. 14/753,322, filed Jun. 29, 2015, which is a divisional of U.S. application Ser. No. 14/164,749, filed Jan. 27, 2014, now U.S. Pat. No. 9,119,399, granted Sep. 1, 2015, which is divisional of U.S. application Ser. No. 13/703,045, filed Jun. 9, 2011, now U.S. Pat. No. 8,691,834, granted Apr. 8, 2014, which is the U.S. national stage of Application No. PCT/EP2011/059572, filed Jun. 9, 2011, which application claims priority from EP 10165463.0, filed Jun. 10, 2010.

The present invention relates to combinations of pyrimethanil, or a salt thereof, and a monoterpene, or a salt thereof, which provide an improved biocidal effect. More particularly, the present invention relates to compositions comprising a combination of pyrimethanil, or a salt thereof, together with a monoterpene selected from thymol and β-thujaplicin in respective proportions to provide a synergistic biocidal effect. Compositions comprising these combinations are useful for the protection of any living or non-living material, such as crops, plants, fruits, seeds, objects made of wood, thatch or the like, engineering material, biodegradable material and textiles against deterioration due to the action of microorganisms such as bacteria, fungi, yeasts, algae, viruses, and the like.

Microorganisms are extremely useful, and even indispensable, in processes such as, e.g. alcoholic fermentation, ripening of cheese, baking of bread, production of penicillin, purification of waste water, production of biogas, and the like. However, microorganisms can also be harmful or highly dangerous; by causing infectious diseases, by forming poisonous or carcinogenic metabolites and by attacking valuable materials, disturbing production processes, or impairment of the quality of products.

Biocides or microbiocides are a broad and diverse group of compounds which are able to control microorganisms: i.e. to eliminate, kill, or inhibit microorganisms, or to reduce the growth or proliferation of microorganisms such as bacteria, fungi, yeasts and algae. An important group of the biocides are the bactericides and fungicides. Since bacteria and fungi occur everywhere, their destructive activity (biodeterioration) is basically unavoidable. Nevertheless objects can be protected with the aid of compounds that prevent the multiplication of bacteria or fungi at the relevant sites, either by killing them or inhibiting their development.

It has now been found that the combination of pyrimethanil (hereinafter referred to as component I) and a monoterpene selected from thymol and β-thujaplicin (hereinafter referred to as a component II), has a synergistic effect on the control of microorganisms.

Pyrimethanil, component (I), is a fungicide with protective and curative action and is used to control grey mould on vines, fruit, vegetables and ornamentals. Pyrimethanil (I) is the generic name for 4,6-dimethyl-N-phenyl-2-pyrimidinamine, which may be represented by the formula

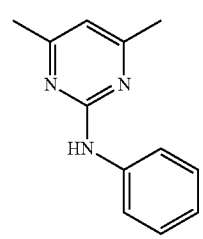

The monoterpene compounds (II) have the following structure:

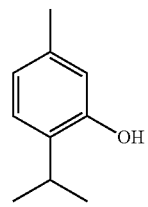

thymol (II-a)
(CAS 89-83-8)

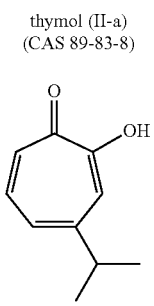

β-thujaplicin (II-b)
(CAS 499-44-5)

Pyrimethanil (I) and the monoterpene compounds (II) may be present in free base form or in the form of an acid addition salt, the latter being obtained by reaction of the base form with an appropriate acid. Appropriate acids comprise, for example, inorganic acids, such as the hydrohalic acids, i.e. hydrofluoric, hydrochloric, hydrobromic and hydroiodic, sulfuric acid, nitric acid, phosphoric acid, phosphinic acid and the like; or organic acids, such as, for example, acetic, propanoic, hydroxyacetic, 2-hydroxypropanoic, 2-oxo-propanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxy-benzoic and the like acids.

The compositions of the present invention have biocidal activity against a broad range of microorganisms such as bacteria, fungi, yeasts and viruses. Bacteria include Gram-positive and Gram-negative bacteria. Fungi include e.g. wood-discoloring fungi, wood-destroying fungi, and phytophatogenic fungi. Virusses include HIV, SARS and bird flue.

The biocidal compositions of the present invention are useful in the preservation of wood, wood products, leather, natural or synthetic textile, fibers, non-wovens, technical textile, plasticized materials and non-plasticized thermoplastics as polypropylene, polyvinylchloride, etc. . . . , paper, wall paper, insulation material, laminates, amino moulding compounds, paints and coatings, fabrics, floor coverings, synthetic fibres like plasticized polymers, hessian, rope and cordage and biodegradable materials and protect said materials against attack and destruction by bacteria or fungi. As wood or wood products which can be preserved with the compositions according to the present invention is considered, for example, wood products such as timber, lumber, railway sleepers, telephone poles, fences, wood coverings, wicker-work, windows and doors, plywood, particle board, waferboards, chipboard, joinery, timber used above ground in exposed environments such as decking and timber used in ground contact or fresh water or salt water environments, bridges or wood products which are generally used in housebuilding, construction and carpentry. As biodegradable materials besides wood which can benefit from treatment with the compositions of the invention include cellulosic material such as cotton.

The biocidal compositions of the present invention are useful in the prevention of microbial contamination or biofilm formation in several industrial processes like gaskets, pipes and tubings in contact with fluids or involved in fluid transport, conveyer belts, surfaces and plastic components used in food transport, processing or production, and medical activities like medical equipment and devices like catheters, pacemakers, implants, surgery equipment and sterile textile.

The biocidal compositions of the present invention are useful in the prevention of hygienic concerns like unwanted bacterial, fungal or algal growth on surfaces, safety problems like the presence of Legionella in closed water systems. Nosocomial infections in hospitals, the presence of Multi-Resistant *Staphylococcus aureus* (MRSA), odor problems like in fabrics like socks, towels, protective uniforms, shoe linings or in filters or floor coverings. The invention is as well possible to protect areas or items coated with an ultra-hygienic polymer like for the manufacture of electrical devices such as light switches and switch plates; sanitary ware such as toilet seats; and door handles, handrails, baby-changing tables, telephones, and other end-use applications where the highest levels of sanitary protection are needed.

The biocidal compositions of the present invention are useful in the prevention of bacterial, fungal or algal growth on surfaces and herewith causing aesthetical problems for the materials considered.

In an embodiment, the present invention relates to a method of controlling microbial growth on wood, wood products and biodegradable materials, which comprises applying an antimicrobially effective amount of a composition comprising a combination of a component (I) and a component (II) in respective proportions to provide a synergistic biocidal effect, to the wood, wood products, leather, natural or synthetic textile, fibers, non-wovens, technical textile, plasticized materials and non-plasticized thermoplastics as polypropylene, polyvinylchloride, etc. . . . , paper, wall paper, insulation material, laminates, amino moulding compounds, paints and coatings, fabrics, floor coverings, synthetic fibres like plasticized polymers, hessian, rope and cordage.

The biocidal compositions of the present invention are also useful to protect engineering materials against microorganisms. Engineering materials which are intended to be protected can be glues, sizes, paints and plastic articles, cooling lubricants, aqueous hydraulic fluids and other non-living materials which can be infested with, or decomposed by, microorganisms.

In an embodiment, the present invention relates to a method of controlling microbial growth on engineering materials, which comprises applying an antimicrobially effective amount of a composition comprising a combination of a component (I) and a component (II) in respective proportions to provide a synergistic biocidal effect, to the engineering materials to be treated.

The biocidal compositions according to the present invention can also be used to protect plants, or parts of plants, e.g. fruit, blossoms, flowers, foliage, stems, roots, cuttings, tubers of plants, fruit and seeds.

As examples of the wide variety of culture plants in which the combinations of components (I) and (II) according to the present invention can be used, there may be named for example cereals, e.g. wheat, barley, rye, oats, rice, sorghum and the like; beets, e.g. sugar beet and fodder beet; pome and stone fruit and berries, e.g. apples, pears, plums, peaches, almonds, cherries, strawberries, raspberries and blackberries; leguminous plants, e.g. beans, lentils, peas, soy beans; oleaginous plants, e.g. rape, mustard, poppy, olive, sunflower, coconut, castor oil plant, cocoa, groundnuts; cucurbitaceae, e.g. pumpkins, gherkins, melons, cucumbers, squashes; fibrous plants, e.g. cotton, flax, hemp, jute; citrus fruit, e.g. orange, lemon, grapefruit, mandarin; vegetables, e.g. spinach, lettuce, asparagus, brassicaceae such as cabbages and turnips, carrots, onions, tomatoes, potatoes, hot and sweet peppers; laurel-like plants, e.g. avocado, cinnamon, camphor tree; or plants such as maize, tobacco, nuts, coffee, sugarcane, tea, vines, hops, bananas, rubber plants, as well as ornamental plants, e.g. flowers, shrubs, deciduous trees and evergreen trees such as conifers. This enumeration of culture plants is given with the purpose of illustrating the invention and not to delimiting it thereto.

In an embodiment, the present invention relates to a method of controlling microbial growth on plants, parts of plants, fruit and seeds, which comprises applying an antimicrobially effective amount of a composition comprising a combination of a component (I) and a component (II) in respective proportions to provide a synergistic biocidal effect, to the plants, parts of plants, fruit and seeds to be treated.

The relative proportions of a component (I) and a component (II) in compositions comprising a combination of a component (I) and a component (II) are those proportions which result in a synergistic biocidal effect, when compared to a composition including, as an active ingredient, either component (I) alone or a component (II) alone. As will be understood by those skilled in the art, the said synergistic effect may be obtained within various proportions of components (I) and (II) in the composition, depending on the kind of microorganism towards which effect is measured and the substrate to be treated. Based on the teachings of the present application, determination of the synergistic effect of such combinations can be performed according to the procedures of the Poison Plate Assay as described in Experiment 1. As a general rule, however, it may be said that for most microorganisms the suitable proportions by weight of the amount of component (I) to component (II) in the active composition should lie in the range from 10:1 to 1:10. Particularly, this range is from 4:1 to 1:4, more particularly from 3:1 to 1:3 or 2:1 to 1:2. Another particular ratio of component (I) to component (II) in the compositions of the present invention is a 1:1 ratio between component (I) and component (II).

The quantity of each of the active ingredients in the compositions according to the present invention will be so that a synergistic biocidal effect is obtained. The concentration of a component (I) and a component (II) in the ready to use compositions is also dependent upon the specific conditions wherein these compositions are used. In particular it is contemplated that the ready to use compositions of the present invention comprise component (I) in a range from 10 to 50.000 mg/l. The component (II) is present in an amount ranging from 10 to 50.000 mg/l or mg/kg.

The compositions according to the present invention comprise a combination of a component (I) and a component (II) in respective proportions to provide a synergistic biocidal effect, and furthermore one or more acceptable carriers.

These carriers are any material or substance with which the composition of components (I) and (II) is formulated in order to facilitate its application/dissemination to the locus to be treated, for instance by dissolving, dispersing, or diffusing the said composition, and/or to facilitate its storage, transport or handling without impairing its antifungal effectiveness. Said acceptable carriers may be a solid or a liquid or a gas which has been compressed to form a liquid including the physical condition described as supercritical fluid, i.e. the compositions of this invention can suitably be used as concentrates, emulsions, emulsifiable concentrates, oil miscible suspension concentrates, oil-miscible liquid, soluble concentrates, solutions, granulates, dusts, sprays, aerosols, pellets, or powders.

In many instances the biocidal compositions to be used directly can be obtained from concentrates, such as e.g. emulsifiable concentrates, suspension concentrates, or soluble concentrates, upon dilution with aqueous or organic media, such concentrates being intended to be covered by the term composition as used in the definitions of the present invention. Such concentrates can be diluted to a ready to use mixture in a spray tank shortly before use. Preferably the compositions of the invention should contain from about 0.01 to 95% by weight of the combination of components (I) and (II). More preferably this range is from 0.1 to 90% by weight. Most preferably this range is from 1 to 80% by weight, depending on the type of formulation to be selected for specific application purposes, as further explained in details hereinafter.

An emulsifiable concentrate is a liquid, homogeneous formulation of the components (I) and (II) to be applied as an emulsion after dilution in water. A suspension concentrate is a stable suspension of the active ingredients in a fluid intended for dilution with water before use. A soluble concentrate is a liquid, homogeneous formulation to be applied as a true solution of the active ingredients after dilution in water.

The biocidal compositions of the present invention can also be formulated as waxes for use as a cover or coating of e.g. fruit, in particular citrus fruit.

In a further embodiment the present invention also relates to a composition only containing a combination of the two active ingredients: i.e. pyrimethanil as a component (I) and as a component (II) a monoterpene compound selected from thymol and β-thujaplicin without further active ingredients being present; and one or more carriers. This also applies to the methods of treatment as described in the present invention. Hence also compositions are covered containing a combination of pyrimethanil as a component (I) and as a component (II) a monoterpene compound selected from thymol and β-thujaplicin; whereby component (I) and component (II) are in respective proportions to provide a synergistic biocidal effect; and one or more carriers. As a general rule, it may be said that the suitable proportions by weight of the amount of component (I) to component (II) in these biocidal compositions should lie in the range from 10:1 to 1:10. Particularly, this range is from 4:1 to 1:4, more particularly from 3:1 to 1:3 or 2:1 to 1:2. The carriers are described hereinbefore.

Biocidal compositions according to the present invention can be of use in post-harvest treatment of fruit, especially citrus fruit. In the latter instance, the fruit will be sprayed with or dipped or drenched into a liquid formulation or the fruit may be coated with a waxy composition. The latter waxy composition conveniently is prepared by thoroughly mixing a suspension concentrate with a suitable wax. The formulations for spray, dip or drench applications may be prepared upon dilution of a concentrate such as, e.g. an emulsifiable concentrate, a suspension concentrate or a soluble liquid, with an aqueous medium. Such concentrate in most instances consists of the active ingredients, a dispersing or suspending agent (surfactant), a thickening agent, a small amount of organic solvent, a wetting agent, optionally some anti-freeze agent, and water.

The biocidal compositions of the present invention can also be used for protecting seed against fungi. To that effect the present fungicidal compositions can be coated on seed, in which case the seed grains are drenched consecutively with a liquid composition of the active ingredients or if they are coated with a previously combined composition. The compositions can also be sprayed or atomised onto the seed using e.g. a spinning disc atomiser.

The combination of components (I) and (II) is preferably applied in the form of compositions wherein both said components are intimately admixed in order to ensure simultaneous administration to the materials to be protected. Administration or application of both components (I) and (II) can also be a "sequential-combined" administration or application, i.e. component (I) and one or more components (II) are administered or applied alternatively or sequentially in the same place in such a way that they will necessarily become admixed together at the locus to be treated. This will be achieved namely if sequential administration or application takes place within a short period of time e.g. within less than 24 hours, preferably less than 12 hours. In case of wood preservation the wood usually needs to be dried between the individual applications thus the period between the sequential applications might be expanded up to several weeks until the solvent used for the first treatment has been evaporated and/or the wood reached the wood moisture content again suitable for the application of the fungicidal formulation. This alternative method can be carried out for instance by using a suitable single package comprising at least one container filled with a formulation comprising the active component (I) and at least one container filled with a formulation comprising an active component (II). Therefore the present invention also encompasses a product containing:

(a) a composition comprising pyrimethanil, or a salt therof, as a component (I); and (b) a composition comprising as a component (II) a monoterpene compound selected from thymol and β-thujaplicin;

as a combination for simultaneous or sequential use, wherein said compositions (a) and (b) are in respective proportions to provide a synergistic biocidal effect. Such products may consist of a suitable package comprising separate containers wherein each container comprises component (I) or component (II), preferably in formulated form.

Such formulated forms in general have the same composition as described for the formulations containing both active ingredients.

Appropriate carriers and adjuvants for use in the compositions of the present invention may be solid or liquid and correspond to suitable substances known in the art of formulation, such as, for example natural or regenerated mineral substances, solvents, dispersants, surfactants, wetting agents, adhesives, thickeners, binders, fertilizers or anti-freeze agents.

Apart from both the aforementioned components (I) and (II), the compositions according to the present invention may further comprise other active ingredients, e.g. other microbiocides, in particular fungicides, and also insecticides, acaricides, nematicides, herbicides, plant growth regulators and fertilizers.

The components (I) and (II) are used in unmodified form or, preferably, together with the adjuvants conventionally employed in the art of formulation. They are therefore formulated following art-known procedures to emulsifiable concentrates, directly sprayable or dilutable solutions, dilute emulsions, wettable powders, soluble powders, dusts, granulates, and also encapsulations in e.g. polymer substances. As with the nature of the compositions, the methods of application, such as spraying, atomizing, dusting, scattering, pouring, smoke generation and thermonebulisation are chosen in accordance with the intended objectives and the prevailing circumstances.

The formulations, i.e. the compositions, preparations or mixtures comprising the active ingredients and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are aromatic hydrocarbons, preferably the fractions containing 8 to 12 carbon atoms, e.g. dimethylbenzene mixtures or substituted naphthalenes, phthalates such as dibutyl phthalate or dioctyl phthalate, aliphatic or alicyclic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethylsulfoxide or dimethylformamide, as well as vegetable oils or epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated absorbent carriers are of the porous type, for example pumice, broken brick, sepiolite or bentonite; and suitable nonsorbent carriers are materials such as calcite or sand. In addition, a great number of pregranulated materials of inorganic or organic nature can be used, e.g. especially dolomite or pulverised plant residues.

Suitable surface-active compounds to be used in the compositions of the present invention are non-ionic, cationic and/or anionic surfactants having good emulsifying, dispersing and wetting properties. The term "surfactants" will also be understood as comprising mixtures of surfactants.

Appropriate carriers and adjuvants for use in the compositions of the present invention may be solid or liquid and correspond to suitable substances known in the art for preparing formulations for treating plants or their loci, or for treating plant products, in particular for treating wood, such as, for example, natural or regenerated mineral substances, solvents, dispersants, surfactants, wetting agents, adhesives, thickeners, binders, fertilizers, anti-freeze agents, repellents, colour additives, corrosion inhibitors, water-repelling agents, siccatives, UV-stabilizers and other active ingredients.

Suitable anionic surfactants can be both water-soluble soaps and water-soluble synthetic surface-active compounds.

Suitable soaps are the alkali metal salts, earth alkaline metal salts or unsubstituted or substituted ammonium salts of higher fatty acids ($C_{10}$-$C_{22}$), e.g. the sodium or potassium salts of oleic or stearic acid, or of natural fatty acid mixtures which can be obtained e.g. from coconut oil or tallow oil. In addition, there may also be mentioned fatty acid methyltaurin salts.

More frequently, however, so-called synthetic surfactants are used, especially fatty sulfonates, fatty sulfates, sulfonated benzimidazole derivatives or alkylarylsulfonates. The fatty sulfonates or sulfates are usually in the form of alkali metal salts, earth alkaline metal salts or unsubstituted or substituted ammonium salts and contain an alkyl radical having from 8 to 22 carbon atoms said alkyl also comprising radicals derived from acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzene sulfonic acid, dibutylnaphthalene-sulfonic acid, or of a naphthalene-sulfonic acid/formaldehyde condensation product. Also suitable are corresponding phosphates, e.g. salts of the phosphoric acid ester of an adduct of p-nonylphenol with 4 to 14 moles of ethylene oxide, or phospholipids.

Non-ionic surfactants are preferably polyglycol ether derivatives of aliphatic or cycloaliphatic alcohols, or saturated or unsaturated fatty acids and alkylphenols, said derivatives containing 3 to 10 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopoly-propylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenol-polyethoxy ethanols, castor oil polyglycol ethers, polypropylene/polyethylene oxide adducts, tributylphenoxypolyethoxyethanol, polyethylene glycol and octylphenoxypolyethoxy-ethanol. Fatty acid esters of polyethylene sorbitan, such as polyoxyethylene sorbitan trioleate, are also suitable non-ionic surfactants.

Particularly advantageous additives useful to improve the application and reduce the dose of the active ingredients, are the natural (animal or plant) or synthetic phospholipids of the cephalin or lecithin type such as, for example, phosphatidylethanolamine, phosphatidylserine, phosphatidylglycerine, lysolecithin, or cardiolipin. Such phospholipids may be obtained from animal or plant cells, in particular from brain-, heart- or liver tissue, egg yolks or soy beans. Appropriate such phospholipids are for instance, phosphatidylchlorin mixtures. Synthetic phospholipids are for instance, dioctanylphosphatidylchloline and dipalmitoylphosphatidylcholine.

EXPERIMENTAL PART

Experiment 1

Poison Plate Assay

Name of component (I): pyrimethanil
Name of component (II): thymol (II-a)
β-thujaplicin (II-b)
Test models: Fungi: to each well of a 24-well microliter plate, 1000 µl of Glucose Agar (GA: 10 g glucose, 1.5 g $K_2HPO_4$, 2 g $KH_2PO_4$, 1 g $(NH_4)_2SO_4$, 0.5 g $MgSO_4$ and 12.5 g agar in 1 liter deionised water) containing the appropriate combination of the test compounds in one of the concentrations of a dose series is added. The nutrient medium is inoculated with the test fungi by adding a sporeimycelium suspension (10 µl) or a small piece of agar from the margin of an actively growing colony and incubated under dark at 27° C. with 70% relative humidity. The growth of the fungi is evaluated after two weeks. Glucose agar is used here instead of PDA (Potato Dextrose Agar), as an alternative, poorer medium for the fungi, in order to increase the chances of detecting activity in compounds like pyrimethanil, which has a mode of action that fungi can easily circumvent on a richer medium (Birchmore et al. 1996, Copping & Hewitt 1998, Fritz et al. 1997).
Concentrations: 300-226-169-127-95-71-53.4-40.1-30.0-22.5-16.9-127 ppm. In addition to this dose series, pyrimethanil single was also tested at 9.50-7.13-5.34-4.01-3.01-2.25-1.69-1.27-0.95-0.71-0.53-0.40 ppm in order to define a lower limit to its activity.

Test combinations:

| % product A | + | % product B |
|---|---|---|
| 100 | + | 0 |
| 80 | + | 20 |
| 66 | + | 33 |
| 50 | + | 50 |
| 33 | + | 66 |
| 20 | + | 80 |
| 0 | + | 100 |

Test species: Fungi:
  *Aureobasidium pullulans* P268
  *Chaetomium globosum* CEB1218.2
  *Cladosporium cladosporioides* B41836
  *Humicola grisea* MG28
  *Stachybotrys atra* CBS328.37
  *Ulocladium atrum* IMI 214669a MIC values (minimum inhibitory concentration in ppm total active ingredient) were noted and synergy was calculated using the Synergy Index method described by Kull et al. (Kull, F. C., P. C. Eismann, H. D. Sylvestrowicz, and R. L. Mayer (1961) "Mixtures of quaternary ammonium compounds and long-chain fatty acids as antifungal agents" *Applied Microbiology* 9: 538-541; also see Zwart Voorspuij, A. J., and C. A. G. Nass (1957) "Some aspects of the notions additivity, synergism and antagonism in the simultaneous activity of two antibacterial agents in vitro" *Arch. intern. Pharmaco-dynamie* 109: 211-228; Steinberg, D. C. (2000) "Measuring synergy" *cosmetics & Toiletries* 115(11): 59-62; and Lada, A., A. N. Petrocci, H. A. Green, and J. J. Merianos (1977) "Antimicrobial composition" U.S. Pat. No. 4,061,750, 3 pp.):

$$\text{Synergy Index } (SI) = \frac{Q_a}{Q_A} + \frac{Q_b}{Q_B}$$

wherein:
  $Q_A$ is the concentration of compound A in ppm, acting alone, which produced an end point (e.g. MIC),
  $Q_a$ is the concentration of compound A in ppm, in the mixture, which produced an end point (e.g. MIC),
  $Q_B$ is the concentration of compound B in ppm, acting alone, which produced an end point (e.g. MIC),
  $Q_b$ is the concentration of compound B in ppm, in the mixture, which produced an end point (e.g. MIC).

When the Synergy Index is greater than 1.0, antagonism is indicated. When the SI is equal to 1.0, additivity is indicated. When the SI is less than 1.0, synergism is demonstrated.

TABLE 1

MIC-values (minimum inhibitory concentration in ppm) and synergy index of combinations of pyrimethanil (component (I)) with thymol (component (II-a))

| | % (I) + % (II-a) | MIC-values in ppm | Synergy Index |
|---|---|---|---|
| *Chaetomium globosum* | 0 + 100 | 71 | — |
| | 80 + 20 | 71 | 0.84 |
| | 66 + 33 | 71 | 0.73 |
| | 50 + 50 | 95 | 0.79 |
| | 33 + 66 | 95 | 0.60 |
| | 20 + 80 | 127 | 0.61 |
| | 100 + 0 | 400 | — |
| *Stachybotrys atra* | 0 + 100 | 95 | — |
| | 80 + 20 | 95 | 0.95 |
| | 66 + 33 | 95 | 0.92 |
| | 50 + 50 | 95 | 0.87 |
| | 33 + 66 | 95 | 0.83 |
| | 20 + 80 | 95 | 0.80 |
| | 100 + 0 | 127 | — |

TABLE 2

MIC-values (minimum inhibitory concentration in ppm) and synergy index of combinations of pyrimethanil (component (I)) with β-thujaplicin (II-b)

| | % (I) + % (II-b) | MIC-values in ppm | Synergy Index |
|---|---|---|---|
| *Ulocladium atrum* | 0 + 100 | 300 | — |
| | 80 + 20 | 40 | 0.45 |
| | 66 + 33 | 40 | 0.67 |
| | 50 + 50 | 23 | 0.54 |
| | 33 + 66 | 30 | 0.90 |
| | 20 + 80 | 23 | 0.82 |
| | 100 + 0 | 23 | — |

The invention claimed is:
1. A method of controlling microbial growth on wood, wood products and biodegrable materials, which comprises applying an antimicrobially effective amount of a composition comprising a combination of pyrimethanil as a component (I) and thymol as a component (II);

whereby component (I) and component (II) are in respective proportions to provide a synergistic biocidal effect, to the wood, wood products and biodegrable materials to be treated.

2. Method of controlling microbial growth on engineering materials, which comprises applying an antimicrobially effective amount of a composition comprising a combination of pyrimethanil as a component (I) and thymol as a component (II);

whereby component (I) and component (II) are in respective proportions to provide a synergistic biocidal effect, to the engineering materials to be treated.

3. Method of controlling microbial growth on plants, parts of plants, fruit and seeds, which comprises applying an antimicrobially effective amount of a composition comprising a combination of pyrimethanil as a component (I) and thymol as a component (II);

whereby component (I) and component (II) are in respective proportions to provide a synergistic biocidal effect, to the plants, parts of plants, fruit and seeds to be treated.

* * * * *